United States Patent [19]

Sakagami et al.

[11] Patent Number: 5,075,299
[45] Date of Patent: * Dec. 24, 1991

[54] CEPHALOSPORIN COMPOUNDS AND ANTIBACTERIAL AGENTS

[75] Inventors: Kenji Sakagami; Katsuyoshi Iwamatsu; Kunio Atsumi; Seiji Shibahara, all of Yokohama, Japan

[73] Assignee: Meiji Seika Kaisha, Ltd., Tokyo, Japan

[*] Notice: The portion of the term of this patent subsequent to Jul. 2, 2008 has been disclaimed.

[21] Appl. No.: 390,580

[22] Filed: Aug. 7, 1989

[30] Foreign Application Priority Data

Aug. 10, 1988 [JP] Japan ................. 63-200652

[51] Int. Cl.$^5$ ................. C07D 501/36; A61K 31/545
[52] U.S. Cl. ................. 514/206; 540/227; 540/225
[58] Field of Search ................. 540/222, 227; 514/206

[56] References Cited

U.S. PATENT DOCUMENTS 4,758,557 7/1988 Tsuruoka et al. ................. 540/227
4,822,786 4/1989 Zama et al. ................. 514/202

Primary Examiner—Nicholas S. Rizzo
Attorney, Agent, or Firm—Jordan and Hamburg

[57] ABSTRACT

Novel cephalosporin compounds represented by formula (I):

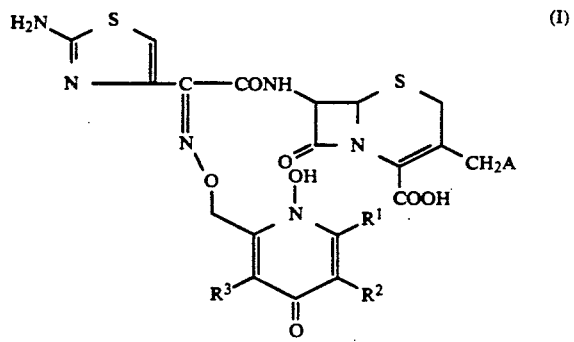

wherein $R^1$ represents a lower alkyl group which may optionally have a substituent; each of $R^2$ and $R^3$ independently represents a hydrogen atom or hydroxy group; and A represents a hydrogen atom or a residue of nucleophilic compound, and pharmacologically acceptable salts or esters thereof exhibit a potent antibacterial activity against gram positive and gram negative bacteria.

15 Claims, No Drawings

CEPHALOSPORIN COMPOUNDS AND ANTIBACTERIAL AGENTS

BACKGROUND OF THE INVENTION

1. Field of the Invention

The present invention relates to novel cephalosporin compounds and pharmacologically acceptable salts or esters thereof as well as antibacterial compositions comprising these compounds as the effective ingredient.

2. Description of Prior Art

Cephalosporin type antibiotics exhibit a wide antibacterial activity against gram positive bacteria and gram negative bacteria. A variety of semi-synthetic cephalosporin compounds are already commercially available and have been provided for use and clinically used as therapeutic agents for various infectious diseases. Among these compounds, however, a few therapeutic agents exert antibacterial activity against *Pseudomonas aeruqinosa* or slime molds. Furthermore, most of these compounds involve shortcomings in that they are unstable to β-lactamase produced by resistant bacteria and have a low activity on resistant bacteria which are currently of concern clinically, etc. (cf., W.E. Wick, Chapter 11 in "Cephalosporins and Penicillins, Chemistry and Biology", edited by E.H. Flynn, Academic Press, New York, N.Y., 1972).

The present inventors previously disclosed in Japanese Patent Application Laid-Open Nos. 492/1987, 10822/1987 and 174083/1987 that cephalosporin compounds having 2-(2-amino-thiazol-4-yl)-2-(1,5-dihydroxy-4-pyridone-2-carboxamido)acetamido group at the 7-position of the cephem ring have a potent activity against pathogenic bacteria over a wide spectrum.

SUMMARY OF THE INVENTION

An object of the present invention is to provide novel cephalosporin compounds which have a wide and potent antibacterial activity against gram positive and gram negative bacteria, exhibit an extremely potent antibacterial activity particularly against *Pseudomonas aeruginosa* and also show a potent antibacterial activity against various β-latamase-producing bacteria, are low in toxicity and have good absorption, and pharmacologically acceptable salts or esters thereof. Another object of the present invention is to provide antibacterial compositions comprising these cephalosporin compounds as the effective ingredient.

The present inventors have paid attention to the (1,5-dihydroxy-4-pyridone) structure bound to a part of the amide side chain at the 7-position of the cephem ring which was previously invented by them and have made further extensive investigations on the structure. As a result, it has been found that the aforesaid objects can be achieved by novel cephalosporin compounds having a (2-substituted-1,5-dihydroxy-4-pyridon-2-ylmethoxyimino) group at the same position and the present invention has thus been accomplished.

The present invention is directed to novel cephalosporin compounds represented by formula (I):

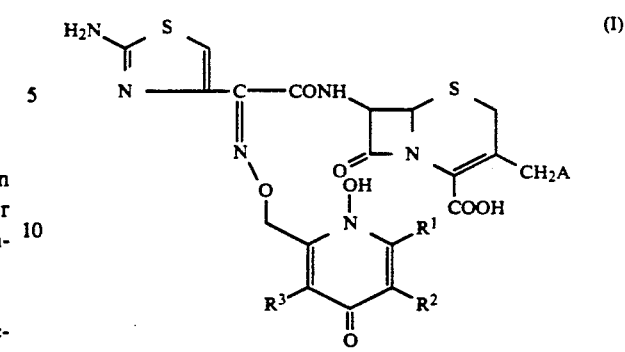

wherein $R^1$ represents a lower alkyl group which may optionally have a substituent; each of $R^2$ and $R^3$ independently represents a hydrogen atom or hydroxy group; and A represents a hydrogen atom or a residue of a nucleophilic compound, and pharmacologically acceptable salts of esters thereof as well as antibacterial compositions comprising these compounds as the effective ingredient.

The compounds of formula (I) are syn-isomers (Z-isomers) and with respect to the pyridone moiety at the 7-substitutent position, the following tautomerism (a) and (b) may be present. The present invention includes both but their nomenclature and structural description are made in terms of pyridone type (a).

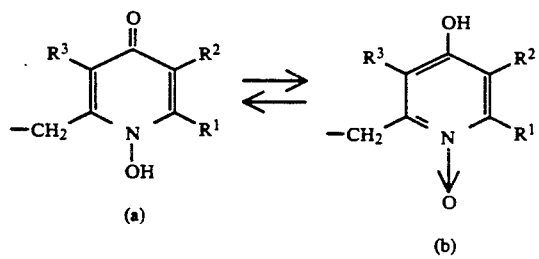

wherein $R^1$, $R^2$ and $R^3$ have the same significance as described above.

DESCRIPTION OF THE PREFERRED EMBODIMENTS

As the pharmacologically acceptable salts of the compound of the present invention represented by formula (I), there may be mentioned medically acceptable salts, especially conventional non-toxic salts such as alkali metal salts, e.g., sodium salts, potassium salts, etc.; alkaline earth metal salts such as calcium salts, magnesium salts, etc.; ammonium salts; salts with organic bases such as organic amine salts, for example, tritylamine salts, pyridine salts, ethanolamine salts, triethanolamine salts, dicyclohexylamine salts, etc. and salts with basic amino acids, e.g., lysine, arginine, etc.

Further as the esters thereof, the group bound to the 4-carboxyl group in the cephalosporin nucleus is a pivaloyloxymethyl group, 1-acetoxyethyl group, 1-ethoxycarbonyloxyethyl group, phthalidyl group, (5-methyl-2-oxo-1,3-dioxol-4-yl)-methyl group, etc.

The group shown by $R^1$ in the compound of formula (I) is a lower alkyl group which may optionally have one or more substituents. Examples of the substituents include hydroxy group, a lower alkoxy group such as methoxy group, ethoxy group, etc.; amino group or a mono- and di-lower alkyl-substituted amino group such as methylamino group dimethylamino group, etc; an acyl group such as formyl group, acetyl group, etc.; a lower alkoxycarbonyl group, carboxyl group, carbamoyl group, cyano group, fluorine atom, chlorine atom, nitro group, sulfonic acid group, sulfonamido group, thiol group, an alkylthio group, an alkylsulfonyl group, an alkylsulfinyl group, etc.

Examples of the residue of nucleophilic compound shown by A include hydroxy group, mercapto group, carbamoyl group, carbamoyloxy group, azido group, a pyridinium group which may optionally have a substituent; a quaternary ammonium group such as quinolinium, isoquinolinium, thiazolinium, etc.; and a heterocyclic ring bound via S, namely, a heterocyclic thio group. The heterocyclic ring as used herein refers to a 5- to 6-membered ring containing 1 to 4 hetero atoms selected from O, S or N and is exemplified by pyridyl, N-oxypyridyl, pyrimidyl, pyridazinyl, N-oxypyridazinyl, pyrazolyl, diazolyl, thiazolyl, thiadiazolyl, oxadiazolyl, triazolyl, tetrazolyl, etc.; and a bicyclic heterocyclic group such as a cycloalkenopyridyl, benzothiazolyl, benzimidazolyl, benzoxazolyl, triazaindolidinyl, etc. These heterocyclic groups may have 1 to 3 substituents thereon, for example, a lower alkyl group, a halogen atom, an alkoxy group, hydroxy group, mercapto group, amino group, carboxyl group, carbamoyl group, a dialkylamino group, carboxymethyl group, a hydroxyalkyl group, a sulfoalkyl group, etc.

The compounds of the present invention represented by formula (I) can be prepared by the following process.

The compounds (1) of the present invention represented by formula (I) can be prepared by reacting compounds represented by the following formula (II):

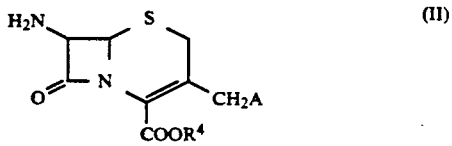

(II)

wherein $R^4$ represents a hydrogen atom or a protective group for carboxyl group and A has the same significance as described above, or reactive derivatives at the amino group thereof or salts thereof with compounds represented by the following formula (III):

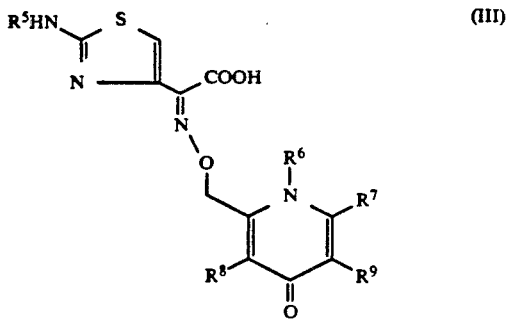

(III)

(wherein $R^5$ represents a hydrogen atom or a protective group for an amino group; $R^6$ represents a splittable protective group such as benzyl group, p-nitrobenzyl group, p-methoxybenzyl group, benzhydryl group, etc.; $R^7$ represents a lower alkyl group which may optionally have a protected substituent; and each of $R^8$ and $R^9$ independently represents a hydrogen atom or a protected hydroxy group) or reactive derivatives at the carboxyl group.

Examples of the reactive derivative of compound (2) shown by formula (II) at the amino group include imino or its tautomeric enamine isomers of Schiff's base formed by the reaction between compound (2) and carbonyl compounds such as an aldehyde, a ketone, etc.; silyl derivatives of compound (2) and bis(trimethylsilyl) acetamide, etc.; derivatives formed by the reaction between compound (2) and phosphorus trichloride or phosgene, etc.

Examples of the salts of compound (2) and compound (3) represented by formula (III) include acid addition salts with organic acids such as acetic acid, maleic acid, tartaric acid, benzenesulfonic acid, toluenesulfonic acid, etc. or with inorganic acids such as hydrochloric acid, hydrobromic acid, sulfuric acid, phosphoric acid, etc.; alkali or alkaline earth metal salts such as sodium salts, potassium salts, calcium salts, magnesium salts, etc.; ammonium salts; organic amine salts, for example, dicyclohexylamine salts, etc.

As the reactive derivatives of compound (3) at the carboxyl group, there may be mentioned acid halides, acid azides, acid anhydrides, activated amides, activated esters, etc. In more detail, mention may be made of acid halides such as acid chlorides, acid bromides, etc.; mixed acid anhydrides of dialkyl phosphates, dibenzyl phosphate, substituted phosphoric acids such as halogenated phosphoric acids, dialkylphosphites, sulfinic acid, thiosulfuric acid, sulfuric acid, alkyl carbonates such as methyl carbonate, ethyl carbonate, etc. with fatty carboxylic acid such as pivalic acid, valeric acid, isovaleric acid, 2-ethylacetic acid, trichloroacetic acid, etc. or with aromatic carboxylic acids such as benzoic acid, etc.; activated amides with imidazole, dimethylpyrazole, triazole, tetrazole, etc.; activated esters such as cyanomethyl esters, methoxymethyl esters, dimethyliminomethyl esters, vinyl esters, propargyl esters, p-nitrophenyl esters, trichlorophenyl esters, 2,4-dinitrophenyl esters, pentachlorophenyl esters, mesylphenyl esters, phenylazophenyl esters, phenylthio esters, p-nitrophenylthio esters, p-cresylthio esters, carboxymethylthio esters, pyranyl esters, pyridyl esters, piperidyl esters, 8-quinolylthio esters, etc. and esters with N-hydroxy compounds such as N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc. These reactive derivatives can be appropriately chosen depending upon the kind of reactant compound (3) to be used.

The reaction between compound (2) and compound (3) is generally carried out in a conventional solvent such as water, acetone, dioxane, acetonitrile, chloroform, methylene chloride, tetrahydrofuran, ethyl acetate, N,N-dimethylformamide, pyridine, etc. or in another organic solvent that does not adversely affect the reaction. These solvents may also be used in admixture with water.

In the case that compound (3) is used in the form of a free acid or base in this reaction, a condensing agent is generally used. Examples of the condensing agent include N,N'-dicyclohexylcarbodiimide, N-cyclohexyl-N'-morpholinoethylcarbodiimide, N-cyclohexyl-N'-(4-diethylaminocyclohexyl)-carbodiimide, N,N'-diethylcarbodiimide, N,N'-diisopropylcarbodiimide, N-ethyl-N'-(3-dimethylaminopropyl)carbodiimide, N,N-carbonylbis(2-mehylimidazole), pentamethyleneketene-N- cyclohexylimine, diphenylketene-N-cyclohexylimine, ethoxyacetylene, a 1-alkoxy-1-chloroethylene, a trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfonyl)-isoxazolium hydroxide intramolecular salt, 1-(p-chlorobenzenesulfonyloxy)-6-chloro-1H-benzotriazole, so-called Vilsmeier's reagent obtained by the reaction between dimethylformamide and thionyl chloride, phosgene, phosphorus oxychloride, etc.; and the like.

The reaction may also be carried out in the presence of an inorganic base or an organic base. Examples of such bases include an alkali metal hydrogencarbonate such as sodium hydrogencarbonate, potassium hydrogencarbonate, etc.; an alkaline earth metal carbonate such as calcium carbonate, etc.; tri-(lower)-alkylamines such as triethylamine, trimethylamine, etc.; pyridine, an N-(lower)-alkylmorpholine, an N,N-di(lower)-alkyl-benzylamine, etc.

The reaction temperature is not particularly limited but the reaction is carried out generally under cooling or with heating.

Furthermore, compound (1) of formula (I) can be prepared by reacting a compound shown by formula (IV):

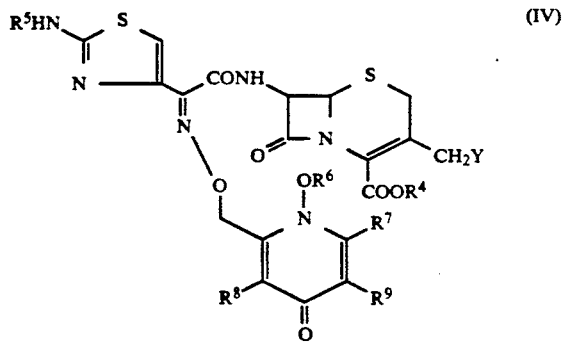

(wherein Y represents acetoxy group or a halogen atom; and $R^5$, $R^6$, $R^7$, $R^8$ and $R^9$ have the same significance as described above) with a nucleophilic compound and then removing the protective group, if necessary. The products obtained by these processes are compound (1) of the present invention or compounds wherein the amino group and carboxyl group and the hydroxy group on the pyridone ring are protected. If necessary and desired, each protective group is removed in a conventional manner. A method for removing the carboxyl protective group and the amino protective group is appropriately chosen. For splitting the amino protective group off, there may be applied known methods such as hydrolysis, reduction and, in the case of the compounds having an acyl group as the protective group, a conventional method which comprises reacting with an iminohalogenating agent and then an iminoetherating agent and then hydrolyzing, if necessary, etc. Hydrolysis using an acid is one of the conventional methods and is applied to the removal of groups, for example, an alkoxycarbonyl group, formyl group, trityl group, etc. As the acid used, formic acid, trifluoroacetic acid, hydrochloric acid, etc. are appropriately chosen depending upon the kind of the amino protective group. The reaction can be carried out in the absence of any solvent or in water, a hydrophilic organic solvent or a solvent mixture thereof. Further in the case of using trifluoroacetic acid, the reaction may also be conducted in the presence of anisole. For splitting the carboxyl protective group off, optional conventional methods such as hydrolysis, reduction, etc. can be used. Hydrolysis using an acid is one of the conventional methods and is applied to removal of, for example, a silyl group, p-methoxybenzyl group, diphenylmethyl group, etc. For splitting the protective group for the hydroxy group on the pyridone ring off, optional conventional methods such as hydrolysis, reduction, etc. can be used. Hydrolysis using an acid or a base is one of the conventional methods. For removing, for example, the p-methoxybenzyl group, diphenylmethyl group, etc., an acid is used and a base is used for removing an acyl group such as acetyl group, benzoyl group, etc.

Compound (1) of formula (I) thus obtained can be separated from the reaction mixture in a conventional manner.

The separation can be achieved by purification with an adsorptive resin such as Amberlite XAD-20 (manufactured by Rohm & Haas Company), Diaion HP-20 or Sepabead SP207 (manufactured by Mitsubishi Chemical Industry Co., Ltd.), etc., precipitation, crystalization and the like in appropriate combination.

The antibacterial composition comprising the compound represented by formula (I), salts or esters thereof as the effective ingredient can be used in various preparation forms such as intravenous and intramuscular injections, etc., oral or rectal agents such as capsules, tablets, powders, etc., oil suppositories, water-soluble suppositories, etc. These various preparations can be prepared in a conventional manner using a carrier, a filler, a binder, a wetting agent, a disintegrator, a surface active agent, a lubricant, a dispersing agent, a buffer, a preservative, a dissolution aid, an antiseptic, a tasting or flavoring agent, a pain alleviator, etc. conventionally used. Specific examples for preparatory forms will be described in detail by referring to the examples hereinafter.

Dose may be appropriately determined depending upon individual case, taking into account condition, age, sex, etc. but a daily dose is generally 250 to 3000 mg per adult and administered one to 4 times a day.

EXAMPLES

The present invention is further described in detail by referring to the following synthesis examples and examples below but is not deemed to be limited thereto. Needless to say, various changes and modifications can be made in the present invention without departing from the spirit and scope of the present invention.

Unless otherwise indicated, NMR data in the examples show δ value obtained using 90 MHz; in the case of measurement in heavy water, the peak of water was made δ value of 4.82 and in the case of other heavy solvent, TMS was made standard.

REFERENCE EXAMPLE 1

2,6-Dihydroxymethyl-5-hydroxy-4-pyrone

Kojic acid, 28 g, was suspended in 100 ml of water and a pH of the suspension was adjusted to 10.5 with 50% sodium hydroxide. After 16 ml of 35% formalin was added to the suspension, the mixture was stirred at room temperature for 3 hours. After completion of the reaction, the reaction mixture was cooled to 5° C. and its pH was adjusted to 2.0 with 50% sulfuric acid. Then, the reaction solution was concentrated to about 50 ml and the resulting crystals were taken out by filtration, washed with a small quantity of chilled water and dried to give 28 g of the title compound.

NMR (DMSO-d6) δ: 4.25 (2H, d, J=7 Hz), 4.35 (2H, d, J=7 Hz), 5.22 (1H, t, J=7 Hz), 5.55 (1H, t, J=7 Hz), 6.22 (1H, s), 6.78 (1H, s),

REFERENCE EXAMPLE 2

6-Methyl-5-hydroxy-2-hydroxymethyl-4-pyrone 2,6-Dihydroxymethyl-5-hydroxy-4-pyrone, 10 g, was added to 50 ml of water to dissolve at 70° C. To the solution was added 8 g of zinc powders and, 28 ml of conc. hydrochloric acid (12 N) was dropwise added to the mixture over an hour. The mixture was stirred at the same temperature for 30 minutes. Insoluble matters (zinc powders) were removed and the reaction solution was cooled to 5° C. After adjusting its pH to 2 with 50% aqueous sodium hydroxide solution, the mixture was stirred at the same temperature for an hour and the resulting crystals were taken out by filtration, washed with a small quantity of chilled water and dried to give 5.15 g of the title compound.

NMR (CDCl3) δ: 2.30 (3H, s), 2.42 (2H, s), 6.45 (1H, s).

REFERENCE EXAMPLE 3

6-Methyl-5-p-methoxybenzyloxy-2-hydroxymethyl-4-pyrone

To a suspension of 5 g of 6-methyl-5-hydroxy-2-hydroxy-4-pyrone in 60 ml of dimethylformamide were successively added 6.8 g of potassium carbonate and 6.2 g of p-methoxybenzyl chloride. The mixture was stirred at 60° C. for 6 hours. After the reaction mixture was concentrated, 200 ml of water and 400 ml of dichloromethane were added to the concentrate. The organic phase was washed with 200 ml of water. After drying over anhydrous magnesium sulfate, the organic phase was concentrated under reduced pressure. The concentrate was separated and purified by flash column chromatography (eluting solution; chloroform: methanol=20:1) using Wako Gel C-300 (manufactured by Wako Pure Chemical Industry Co., Ltd.) (100 g) to give 5.3 g of the title compound.

NMR (CDCl3) δ: 2.05 (3H, s), 3.75 (3H, s), 4.38 (2H, s), 5.0 (2H, s), 6.40 (1H, s), 6.75 7.25 (4H, ABq, J=9 Hz).

REFERENCE EXAMPLE 4

6-Methyl-5-p-methoxybenzyloxy-2-hydroxymethyl-1-hydroxy-4-pyridone

To a solution of 4 g of 6-methyl-5-p-methoxybenzyloxy-2-hydroxymethyl-4-pyrone in 50 ml of pyridine was added 5 g of hydroxylamine hydrochloride at room temperature. The mixture was stirred at 70° to 75° C. for 7 hours. After the reaction liquid was concentrated under reduced pressure, the residue was dissolved in 600 ml of chloroform and washed in succession with water and saturated aqueous sodium hydrogencarbonate solution. After drying the chloroform layer over anhydrous magnesium sulfate, the organic phase was dried and concentrated under reduced pressure. The concentrate was separated and purified by flash column chromatography (eluting solution; chloroform: methanol=20:1) using Wako Gel C-300 (manufactured by Wako Pure Chemical Industry Co., Ltd.) (100 g) to give 1.3 g of the title compound.

NMR (CDCl3) δ: 2.25 (3H, s), 3.75 (3H, s), 4.62 (2H, s), 4.95 (2H, s), 6.80, 7.25 (4H, ABq, J=9 Hz), 7.52 (1H, s).

REFERENCE EXAMPLE 5

6-Methyl-5-p-methoxybenzyloxy-2-hydroxymethyl-1-diphenylmethyloxy-4-pyridone

To a solution of 1 g of 6 methyl-5-p-methoxybenzyloxy-2-hydroxymethyl-1-hydroxy-4-pyridone in 60 ml of dimethylformamide were successively added 710 mg of potassium carbonate and 1.3 g of diphenylmethyl bromide. The mixture was stirred at room temperature for 17 hours. After completion of the reaction, the reaction liquid was concentrated and the concentrate was added to 20 ml of water and 40 ml of dichloromethane. The organic phase was washed with 20 ml of water. After drying over anhydrous magnesium sulfate, the organic phase was concentrated under reduced pressure. The concentrate was separated and purified by flash column chromatography (eluting solution; chloroform: methanol=20:1) using Wako Gel C-300 (100 g) to give 1.35 g of the title compound.

NMR (CDCl3) δ: 1.72 (3H, s), 3.72 (3H, s), 5.05 (2H, s), 5.92 (1H, s), 6.48 (1H, s), 6.76, 7.24 (4H, ABq, J=9 Hz), 7.20 (10H, m).

REFERENCE EXAMPLE 6

6-Methyl-5-p-methoxybenzyloxy-2-phthalimidoxymethyl-1-diphenylmethyloxy-4-pyridone In 50 ml of dry tetrahydrofuran, 1.3 g of 6-methyl-5-p-methoxybenzyloxy-2-hydroxymethyl-1-diphenylmethyloxy-4-pyridone was dissolved and 465 mg of N-hydroxyphthalimide and 1.12 g of triphenylphosphine were added to the solution. The reaction liquid was cooled to 5° C. and 10 ml of tetrahydrofuran solution containing 744 mg of diethyl azodicarboxylate was dropwise added thereto over 10 minutes. The mixture was stirred at the same temperature for 10 minutes. After completion of the reaction, the reaction liquid was concentrated to about 20 ml and 50 ml of water and 100 ml of dichloromethane were added to the concentrate. The organic phase was washed with 20 ml of water. After drying over anhydrous magnesium sulfate, the organic phase was concentrated under reduced pressure. The concentrate was separated and purified by flash column chromatography (eluting solution; chloroform: methanol=20:1) using Wako Gel C-300 (100 g) to give 1.33 g of the title compound.

NMR (CDCl3) δ: 1.72 (3H, s), 3.76 (3H, s), 4.54 (2H, s), 5.10 (2H, s), 6.20 (1H, s), 6.30 (1H, s), 6.82, 7.25 (4H, ABq, J=9 Hz), 7.30 (10H, m), 7.72 (4H, m).

REFERENCE EXAMPLE 7

(Z)-2-(2-Tritylaminothiazol-4-yl)-2-(6-methyl-5-p-methoxybenzyloxy-1-diphenylmethyloxy-4-pyridon-2-ylmethoxyimino)acetic acid In 30 ml of dichloromethane was dissolved 1.2 g of 6-methyl-5-p-methoxybenzyloxy-2-phthalimidoxymethyl-1-diphenylmethyloxy-4-pyridone. The solution was cooled to 5° C. After 110 mg of hydrazine monohydrate was added to the solution, the mixture was stirred at the same temperature for an hour.

Insoluble matters were removed and the filtrate was concentrated to dryness. To the residue were added 20 ml of chloroform and 10 ml of ethanol to dissolve and, 830 mg of 2-oxo-2-(2-tritylaminothiazol-4-yl)acetic acid was added to the solution. The mixture was stirred at room temperature for 17 hours. After completion of the reaction, the reaction solution was filtered and the filtrate was concentrated to dryness. To the residue was added ether to cause crystallization. The formed crystals were taken out by filtration and dried under reduced pressure to give 1.3 g of the title compound.

NMR (CDCl$_3$) δ: 1.60 (3H, s), 3.62 (3H, s), 4.90 (4H, bs), 6.06 (1H, s), 6.46 (1H, s), 6.65, 7.30 (4H, ABq, J=9 Hz), 7.20 (25H, m).

REFERENCE EXAMPLE 8

5-p-Methoxybenzyloxy-2-hydroxymethyl-4-pyrone

Kojic acid, 42.6 g, was dissolved in 350 ml of dimethylformamide and 82.8 g of anhydrous potassium carbonate and 55 g of p-methoxybenzyl chloride were added to the solution. The reaction was carried out at 70° to 75° C. for 1.5 hours.

After completion of the reaction, the reaction liquid was concentrated to approximately half and the concentrate was dropwise added to 700 ml of cooling water. The formed precipitates were taken out by filtration, washed with water and ethyl acetate and dried to give 59.9 g of the title compound.

NMR (CDCl$_3$) δ: 3.80 (3H, s), 4.43 (2H, s), 4.96 (2H, s), 6.50 (1H, s), 6.68 (2H, d), 7.30 (2H, d), 7.51 (1H, s).

REFERENCE EXAMPLE 9

5-p-Methoxybenzyloxy-2-chloromethyl-4-pyrone 5-p-Methoxybenzyloxy-2-hydroxymethyl-4-pyrone, 24 g, was dissolved in 120 ml of dry tetrahydrofuran. The solution was cooled to 5° C. and 15 ml of thionyl chloride was dropwise added to the solution over 30 minutes. The reaction solution was stirred at the same temperature for 3 hours. After completion of the reaction, the reaction liquid was concentrated to approximately 20 ml and the concentrate was added to 50 ml of water and 100 ml of dichloromethane. Under ice cooling, the pH was adjusted to 7.0 with saturated sodium hydrogencarbonate aqueous solution and the organic phase was washed with 20 ml of water. After drying over anhydrous magnesium sulfate, the organic phase was concentrated under reduced pressure and crystallized with ethyl acetate-ether. The formed crystals were taken out by filtration and dried under reduced pressure to give 20 g of the title compound.

NMR (CDCl$_3$) δ: 3.75 (3H, s), 4.20 (2H, s), 4.92 (2H, s), 6.40 (1H, s), 6.82, 7.26 (4H, ABq, J=9 Hz), 7.48 (1H, s).

REFERENCE EXAMPLE 10

5-p-Methoxybenzyloxy-2-methyl-4-pyrone 5-p-Methoxybenzyloxy-2-chloromethyl-4-pyrone, 10 g, was dissolved in 100 ml of acetone and, 5.5 g of sodium iodide and 11.6 g of triphenylphosphine were added to the solution followed by stirring at room temperature for 3 hours. After completion of the reaction, the reaction liquid was concentrated to dryness and the residue was added to 50 ml of water and 100 ml of dichloromethane. Under ice cooling, the pH was adjusted to 7.0 with saturated sodium hydrogencarbonate aqueous solution and the mixture was stirred at the same temperature for 30 minutes. The organic phase was washed with 20 ml of water. After drying over anhydrous magnesium sulfate, the organic phase was concentrated under reduced pressure and purified by flash column chromatography (eluting solution; chloroform: methanol=20:1) using Wako Gel C-300 (500 g) to give 8.2 g of the title compound.

NMR (CDCl$_3$) δ: 2.20 (3H, s), 3.75 (3H, s), 4.95 (2H, s), 6.15 (1H, s), 6.82, 7.28 (4H, ABq, J=9 Hz), 7.70 (1H, s).

REFERENCE EXAMPLE 11

5-Hydroxy-2-methyl-4-pyrone 5-p-Methoxybenzyloxy-2-methyl-4-pyrone, 10 g, was dissolved in 10 ml of anisole and 15 ml of trifluoroacetic acid was dropwise added to the solution under ice cooling. After stirring at the same temperature for 3 hours, the mixture was concentrated under reduced pressure. The concentrate was separated and purified by flash column chromatography (eluting solution; chloroform: methanol=20:1) using Wako Gel C-300 (200 g) to give 2.4 g of the title compound.

NMR (CDCl$_3$) δ: 2.25 (3H, s), 6.22 (1H, s), 7.72 (1H, s).

REFERENCE EXAMPLE 12

5-Hydroxy-2-methyl-4-pyrone

Kojic acid, 30 g, as added to 150 ml of water and dissolved at 70° C. To the solution was added 30 g of zinc powders and, 90 ml of conc. hydrochloric acid (12 N) was dropwise added to the mixture over 2 hours. The mixture was stirred at the same temperature for 30 minutes. Insoluble matters (zinc powders) were removed and the reaction liquid was cooled to 5° C. After adjusting its pH to 2 with 50% aqueous sodium hydroxide solution, the mixture was concentrated under reduced pressure and the residue was dissolved in 100 ml of dichloromethane. The solution was washed with water (100 ml, 3 times). After drying over anhydrous magnesium sulfate, the system was separated and purified by flash column chromatography (eluting solution; chloroform: methanol=20:1) using Wako Gel C-300 (200 g) to give 2.4 g of the title compound as crystals. Physical data of this compound were identical with those of the compound obtained in Reference Example 11.

REFERENCE EXAMPLE 13

6-Hydroxymethyl-5-hydroxy-2-methyl-4-pyrone

5-Hydroxy-2-methyl-4-pyrone, 6 g, was suspended in 25 ml of water and a pH of the suspension was adjusted to 10.5 with 50% sodium hydroxide. After 5 ml of 35% formalin was added to the suspension, the mixture was stirred at room temperature for 3 hours. After completion of the reaction, the reaction mixture was cooled to 5° C. and its pH was adjusted to 2.0 with 50% sulfuric acid. Then, the reaction solution was concentrated to about half and the resulting crystals were taken out by filtration and washed with a small quantity of chilled water to give 5.9 g of the title compound.

NMR (CDCl$_3$) δ: 2.28 (3H, s), 4.52 (2H, s), 6.10 (1H, s).

REFERENCE EXAMPLE 14

6-Hydroxymethyl-5-p-methoxybenzyloxy-2-methyl-4-pyrone

To a suspension of 5.9 g of 6-hydroxymethyl-5-hydroxy-2-methyl-4-pyrone in 60 ml of dimethylformamide were successively added 6.2 g of potassium carbonate and 6.2 ml of p-methoxybenzyl chloride. The mixture was stirred at 70° C. for 2 hours. The reaction liquid was concentrated and 200 ml of water and 400 ml of dichloromethane were added to the concentrate. The organic phase was then washed with 200 ml of water. After drying over anhydrous magnesium sulfate, the organic phase was concentrated under reduced pressure. The concentrate was then separated and purified by flash column chromatography (eluting solution; chloroform: methanol=20:1) using Wako Gel C-300 (300 g) to give 5.9 g of the title compound.

NMR (CDCl$_3$) δ: 2.2 (3H, s), 3.70 (3H, s), 4.25 (2H, d, J=7 Hz), 5.10 (2H, s), 6.12 (1H, s), 6.82, 7.25 (4H, ABq, J=9 Hz).

REFERENCE EXAMPLE 15

6-Hydroxymethyl-5-p-methoxybenzyloxy-2-methyl-1-hydroxy-4-pyridone

To a solution of 4 g of 6-hydroxymethyl-5-p-methoxybenzyloxy-2-methyl-4-pyrone in 50 ml of pyridine was added 5 g of hydroxylamine hydrochloride at room temperature. The mixture was stirred at 70° to 75° C. for 7 hours. After the reaction liquid was concentrated under reduced pressure, the residue was dissolved in 200 ml of chloroform and washed in succession with water, 5% cold hydrochloric acid and saturated aqueous sodium hydrogencarbonate solution. After drying over anhydrous magnesium sulfate, the chloroform layer was dried and concentrated under reduced pressure. The concentrate was separated and purified by flash column chromatography (eluting solution; chloroform: methanol=20:1) using Wako Gel C-300 (100 g) to give 350 mg of the title compound.

NMR (DMSO-d6) δ: 2.25 (3H, s), 3.70 (3H, s), 4.45 (2H, s), 5.92 (2H, s), 6.75 (2H, s), 6.85, 7.25 (4H, ABq, J=9 Hz).

REFERENCE EXAMPLE 16

6-Hydroxymethyl-5-p-methoxybenzyloxy-2-methyl-1-diphenylmethyloxy-4-pyridone

To a solution of 300 mg of 6-hydroxymethyl-5-p-methoxybenzyloxy-2-methyl-1-hydroxy-4-pyridone in 10 ml of dimethylformamide were successively added 213 mg of potassium carbonate and 423 mg of diphenylmethyl bromide. The mixture was stirred at room temperature for 2 hours. After completion of the reaction, the reaction liquid was concentrated and the concentrate was added to 20 ml of water and 40 ml of dichloromethane. The organic phase was washed with 20 ml of water.

After drying over anhydrous magnesium sulfate, the organic phase was concentrated under reduced pressure. The concentrate was then separated and purified by flash column chromatography (eluting solution; chloroform: methanol=20:1) using Wako Gel C-300 (80 g) to give 428 mg of the title compound.

NMR (CDCl$_3$) δ: 1.70 (3H, s), 3.72 (3H, s), 4.20 (2H, bs), 5.30 (2H, s), 6.0 (1H, s), 6.12 (1H, s), 6.8 (2H, ABq, J=9 Hz), 7.2 (12H, m).

REFERENCE EXAMPLE 17

6-Phthalimidoxymethyl-5-p-methoxybenzyloxy-2-methyl-1-diphenylmethyloxy-4-pyridone In 10 ml of dry tetrahydrofuran, 367 mg of 6-hydroxymethyl-5-p-methoxybenzyloxy-2-methyl-1-diphenylmethoxy-4-pyridone was dissolved and 200 mg of N-hydroxy-phthalimide and 313 mg of triphenylphosphine were added to the solution. The reaction liquid was cooled to 5° C. and 5 ml of tetrahydrofuran solution containing 210 mg of diethyl azodicarboxylate was dropwise added thereto over 10 minutes. The mixture was stirred at the same temperature for 30 minutes. After completion of the reaction, the reaction liquid was concentrated and the concentrate was added to 25 ml of water and 50 ml of dichloromethane. The organic phase as washed with 20 ml of water. After drying over anhydrous magnesium sulfate, the organic phase was concentrated under reduced pressure. The concentrate was then separated and purified by flash column chromatography (eluting solution; chloroform: methanol=20:1) using Wako Gel C-300 (100 g) to give 450 mg of the title compound.

NMR (CDCl$_3$) δ: 1.90 (3H), s), 3.72 (3H, s), 4.92 (2H, s), 4.96 (2H, s), 6.0 (1H, s), 6.55 (1H, s), 6.70, 7.10 (4H, ABq, J=9 Hz), 6.85 (1H, m), 7.2–7.75 (14H, m).

REFERENCE EXAMPLE 18

(Z)-2-(2-Tritylaminothiazol-4-yl)-2-(5-p-methoxybenzyloxy-2-methyl-1-diphenylmethyloxy-4-pyridon-6-ylmethoxyimino)acetic acid In 30 ml of dichloromethane was dissolved 450 mg of 6-phthalimidoxymethyl-5-p-methoxybenzyloxy-2-methyl-1-diphenylmethyloxy-4-pyridone. The solution was cooled to 5° C. After 40 mg of hydrazine monohydrate was added to the solution, the mixture was stirred at the same temperature for an hour. Insoluble matters were removed and the filtrate was concentrated to dryness. To the residue were added 10 ml of chloroform and 5 ml of ethanol to dissolve and, 330 mg of 2-oxo-2-(2-aminothiazol-4-yl)acetic acid was added to the solution. The mixture was stirred at room temperature for 17 hours. After completion of the reaction, the reaction solution was filtered and the filtrate was concentrated to dryness. To the residue was added isopropyl ether to cause crystallization. The formed crystals were taken out by filtration and dried under reduced pressure to give 830 mg of the title compound.

NMR (CDCl$_3$) δ: 1.50 (3H, s), 3.65 (3H, s), 4.95 (2H, s), 5.05 (2H, s), 6.35 (1H, s), 6.55 (2H, ABq, J=9 Hz), 6.72 (1H, s), 7.2–7.7 (26H, m).

REFERENCE EXAMPLE 19

6-Morpholinomethyl-5-hydroxy-2-hydroxymethyl-4-pyrone

In 70 ml of ethanol were dissolved 7 g of morpholine and 6.4 ml of 35% formalin followed by stirring at room temperature for 30 minutes. Further, 8.3 g of kojic acid was added thereto and stirred for 30 minutes in the same temperature. The formed crystals were taken out by filtration, washed in succession with ethanol and ether and dried to give 11.5 g of the title compound.

NMR (DMSL-d6): 2.30–2.62 (4H, m), 3.40–3.60 (6H, m), 4.30 (2H, s), 5.6 (1H, bs), 6.32 (1H, s), 8.8 (1H, bs).

REFERENCE EXAMPLE 20

6-Morpholinomethyl-5-p-methoxybenzyloxy-2-hydroxymethyl-4-pyrone

To a suspension of 5.45 g of 6-morpholinomethyl-5-hydroxy-2-hydroxymethyl-4-pyrone in 50 ml of dimethylformamide were successively added 3.32 g of potassium carbonate and 4 ml of p-methoxybenzyl chloride. The mixture was stirred at 70° C. for 4 hours and at room temperature for a further 17 hours. The reaction liquid was concentrated and 100 ml of water and 200 ml of dichloromethane were added to the concentrate. The organic phase was then washed with 100 ml of water. After drying over anhydrous magnesium sulfate, the organic phase was concentrated under reduced pressure. The concentrate was then separated and purified by flash column chromatography (eluting solution; chloroform: methanol=20:1) using Wako Gel C-300 (200 g) to give 1.8 g of the title compound.

NMR (CDCl$_3$) δ: 2.30–2.45 (4H, m), 3.30 (2H, s), 3.50–3.65 (4H, m), 3.72 (3H, s), 4.40 (2H, s), 5.10 (2H, s), 6.40 (1H, s), 6.75, 7.25 (4H, ABq, J=9 Hz).

EXAMPLE 1 p-Methoxybenzyl 7-((Z)-2-(2-tritylaminothiazol-4-yl)-2-(6-methyl-5-p-methoxybenzyloxy-1-diphenylmethyloxy-4-pyridon-2-yl-methoxyimino)acetamido)-3-(1,2,3-thiadiazol-5-ylthiomethyl)-3-cephem-4-carboxylate In 20 ml of dichloromethane were dissolved 433 mg of (Z)-2-(2-tritylaminothiazol-4-yl)-2-(6-methyl-5-p-methoxybenzyloxy-1-diphenylmethyloxy-4-pyridon-2-ylmethoxyimino)acetic acid, 80 mg of hydroxybenztriazole monohydrate and 255 mg of p-methoxybenzyl 7-amino-3-(1,2,3-thiadiazol-5-ylthiomethyl)-3-cephem-4-carboxylate and 103 mg of dicyclohexylcarbodiimide was added to the solution. The mixture was stirred at room temperature for 17 hours. After completion of the reaction, insoluble matters were removed and the reaction liquid was concentrated to dryness under reduced pressure. The residue was separated and purified by flash column chromatography (eluting solution; chloroform: methanol=20:1) using Wako Gel C-300 (50 g) to give 210 mg of the title compound.

NMR (CDCl$_3$) δ: 1.72 (3H, s), 3.40 (2H, bs), 3.72 (3H, s), 3.76 (3H, s), 3.85, 4.25 (2H, ABq, J=14 Hz), 4.85 (1H, d, J=5 Hz), 5.65 (1H, dd, J=5 Hz, 9 Hz), 5.05 (2H, s), 5.08 (2H, s), 5.8 (2H, d, J=5 Hz), 6.2 (1H, s), 6.32 (1H, s), 6.50 (1H, s), 6.6–7.3 (24H, m).

EXAMPLE 2

7-((Z)-2-(2-Aminothiazol-4-yl)-2-(6-methyl-1,5-dihydroxy-4-pyridon-2-ylmethoxyimino)acetamido)-3-(1,2,3-thiadiazol-5-yl-thiomethyl)-3-cephem-4-carboxylic acid In 1 ml of anisole was dissolved 210 mg of p-methoxybenzyl 7-((Z)-2-(2-tritylaminothiazol-4-yl)-2-(6-methyl-5-p-methoxybenzyloxy-1-diphenylmethyloxy-4-pyridon-2-yl-methoxyimino)acetamido)-3-(1,2,3-thiadiazol-5-ylthiomethyl)-3-cephem-4-carboxylate and 2 ml of trifluoroacetic acid was dropwise added to the solution under ice cooling. After stirring at the same temperature for an hour, 40 ml of ice- cooled isopropyl ether was added to the mixture. The formed precipitates were taken out by filtration and dried under reduced pressure. The precipitates were suspended in 1 ml of water and 7% sodium hydrogencarbonate aqueous solution was added to the suspension under ice cooling to adjust its pH to 7.5 to make a solution. The solution was purified by column chromatography (eluting solution; water, 30% methanolic water) using 20 ml of DIAION HP20 resin to give 52 mg of the title compound as the sodium salt.

NMR (D$_2$O) δ: 2.36 (3H, s), 3.20, 3.65 (2H, ABq, J=18 Hz), 3.95, 4.36 (2H, ABq, J=14 Hz), 5.10 (1H, d, J=5 Hz), 5.25, 5.45 (2H, ABq, J=10 Hz), 5.75 (1H, d, J=5 Hz), 6.72 (1H, s), 7.08 (1H, s), 8.72 (1H, s).

EXAMPLE 3

Diphenylmethyl 7-((Z)-2-(2-tritylaminothiazol-4-yl)-2-(6-methyl-5-p-methoxybenzyloxy-1-diphenylmethyloxy-4-pyridon-2-yl-methoxyimino)acetamido)-3-(1-methyl-1H-tetrazol-5-ylthiomethyl)-3-cephem-4-carboxylate In a manner similar to Example 1, 230 mg of the title compound was obtained from 433 mg of (Z)-2-(2-tritylamino-thiazol-4-yl) -2-(6-methyl-5-p-methoxybenzyloxy-1-diphenylmethyloxy-4-pyridon-2-ylmethoxyimino)acetic acid and 522 mg of diphenylmethyl 7-amino-3-(1-methyl-1H-tetrazol-5-ylthiomethyl)-3-cephem-4-carboxylate.

NMR (CDCl$_3$) δ: 1.72 (3H, s), 3.62 (2H, s), 3.70 (3H, s), 3.75 (3H, s), 4.15, 4.42 (2H, ABq, J=14 Hz), 4.95 (1H, d, J=5 Hz), 5.05 (2H, s), 5.80 (1H, dd, J=5 Hz, J=9 Hz), 5.85 (2H, s), 6.35 (1H, s), 6.65 (1H, s), 6.75 (2H, ABq, J=9 Hz), 6.82 (1H, s), 7.1–7.5 (27H, m.

EXAMPLE 4

7-((Z)-2-(2-Aminothiazol-4-yl)-2-(6-methyl-1,5-dihydroxy-4-pyridon-2-ylmethoxyimino)acetamido)-3-(1-methyl-1H-tetrazol-5-ylthiomethyl)-3-cephem-4-carboxylic acid In 1 ml of anisole was dissolved 200 mg of diphenylmethyl 7-[(Z)-2-(2-tritylaminothiazol-4-yl)-2-(6-methyl-5-p-methoxybenzyloxy-1-diphenylmethyloxy-4-pyridon-2-ylmethoxyimino)acetamido]-3-(1-methyl-1H-tetrazol-5-ylthiomethyl)-3-cephem-4-carboxylate and 2 ml of trifluoroacetic acid was dropwise added to the solution under ice cooling. After stirring at the same temperature for an hour, 40 ml of ice-cooled isopropyl ether was added to the mixture. The formed precipitates were taken out by filtration and dried under reduced pressure. The precipitates were suspended in 1 ml of water and 7% sodium hydrogencarbonate aqueous solution was added to the suspension under ice cooling to adjust its pH to 7.5 to make a solution. The solution was purified by column chromatography (eluting solution; water, 30% methanolic water) using 20 ml of DIAION HP20 resin to give 65 mg of the title compound as the sodium salt.

NMR (D$_2$O) δ, 400 Mz: 2.3 (3H, s), 3.1, 3.6 (2H, ABq, J=20 Hz), 4.0, 4.3 (2H, ABq, J=12 Hz), 5.1 (1H, d, J=5 Hz), 5.25, 5.4 (2H, ABq, J=12 Hz), 5.72 (1H, d, J=5 Hz), 6.7 (1H, s), 7.1 (1H, s),

EXAMPLE 5 p-Methoxybenzyl 7-[(Z)-2-(2-tritylaminothiazol-4-yl)-2-(5-p-methoxybenzyloxy-2-methyl-1-diphenylmethyloxy-4-pyridon-6-yl-methoxyimino)acetamido]-3-(1,2,3-thiadiazol-5-ylthiomethyl)-3-cephem-4-carboxylate In 20 ml of dichloromethane were dissolved 433 mg of (Z)-2-(2-tritylaminothiazol-4-yl)-2-(5-p-methoxybenzyloxy-2-methyl-1-diphenylmethyloxy-4-pyridon-6-ylmethoxyimino)acetic acid, 80 mg of hydroxybenztriazole monohydrate and 255 mg of p-methoxybenzyl 7-amino-3-(1,2,3-thiadiazol-5-ylthiomethyl)-3-cephem-4-carboxylate and 103 mg of dicyclohexylcarbodiimide was added to the solution. The mixture was stirred at room temperature for 17 hours. After completion of the reaction, insoluble matters were removed and the reaction liquid was concentrated to dryness under reduced pressure. The residue was separated and purified by flash column chromatography (eluting solution; chloroform: methanol=20:1) using Wako Gel C-300 (50 g) to give 200 mg of the title compound.

NMR (CDCl$_3$) δ: 1.60 (3H, s), 3.25, 3.45 (2H, ABq, J=18 Hz), 3.65 (3H, s), 3.72 (H, s), 3.90, 4.25 (2H, ABq, J=14 Hz), 4.82 (1H, d, J=5 Hz), 5.05 (2H, s), 5.15 (2H, s), 5.50 (1H, dd, J=5 Hz, J=9 Hz), 5.95 (2H, s), 6.25 (1H, s), 6.6–7.3 (37H, m).

EXAMPLE 6

7-[(Z)-2-(2-aminothiazol-4-yl)-2-(1,5-dihydroxy-2-methyl-4-pyridon-6-ylmethoxyimino)acetamido]-3-1,2,3-thiadiazol-5-ylthiomethyl)-3-cephem-4-carboxylic acid In 0.2 ml of anisole was dissolved 200 mg of p-methoxybenzyl 7-[(Z)-2-(2-tritylaminothiazol-4-yl)-2-(5-p-methoxybenzyloxy-2-methyl-1-diphenylmethyloxy-4-pyridon-6-ylmethoxyimino)acetamido]-3-(1,2,3-thiadiazol-5-ylthiomethyl)-3-cephem-4-carboxylate and 2 ml of trifluoroacetic acid was dropwise added to the solution under ice cooling. After stirring at the same temperature for an hour, 40 ml of ice-cooled isopropyl ether was added to the mixture. The formed precipitates were taken out by filtration and dried under reduced pressure. The precipitates were suspended in 1 ml of water and 7% sodium hydrogencarbonate aqueous solution was added to the suspension under ice cooling to adjust its pH to 7.5 to make a solution. The solution was purified by column chromatography (eluting solution; water, 30% methanolic water) using 20 ml of DIAION HP20 resin to give 39 mg of the title compound as the sodium salt.

NMR (D$_2$O) δ, 400 Mz: 2.25 (3H, s), 3.1, 3.6 (2H, ABq, J=20 Hz), 4.0, 4.3 (2H, ABq, J=16 Hz), 5.1 (1H, d, J=5 Hz), 5.5 (2H, s), 5.7 (1H, d, J=5 Hz), 6.5 (1H, s), 7.1 (1H, s), 8.7 (1H, s).

EXAMPLE 7

Preparation of dry powders for injection

10% Aqueous solution of the compound of Example 2 is aseptically filtered and 1.0 g of the solution was charged in a vial for injection. The vial containing the solution is freeze dried. Then, the upper portion of the vial is aseptically covered with a stopper and the upper portion is wound and fastened with aluminum. Upon use, distilled water for injection is poured through the rubber stopper using a syringe and the powders are dissolved therein. The solution is used as an injection.

EXAMPLE 8

Preparation of capsules

| Compound of Example 2 | 250 parts (titer) |
| Lactose | 60 parts |
| Magnesium stearate | 5 parts |

The above composition is uniformly mixed and the mixture is charged in capsules of 250 mg (titer)/capsule.

Acute toxicity of the compound of Example 2 was examined using mice. As the result, no death was noted in a dose of 2 g/kg by intravenous injection.

The compounds of the present invention represented by formula (I) and salts thereof are novel compounds and exhibit a high antibacterial activity that can inhibit growth of pathogenic microorganisms over a wide area, including gram positive and negative bacteria. In order to demonstrate the utility of the compounds of the present invention, antibacterial activity of some of the compounds measured by the agar dilution method is shown in Table 1.

TABLE 1

| | Antibacterial Activity MIC (μg/ml) | | | | |
|---|---|---|---|---|---|
| Bacteria Tested | Compound of Example 2 | Compound of Example 4 | Compound of Example 6 | Comparison CAZ | Comparison CTX |
| *Staphylococcus aureus* 606 E-25 | 12.5 | 25 | 1.56 | 12.5 | 1.56 |
| *Escherichia coli* W3630 RGN238 | <0.025 | <0.025 | 0.05 | 0.39 | 0.20 |
| *Escherichia coli* GN206 | 0.39 | 0.10 | 0.78 | 1.56 | 1.56 |
| *Klebsiella pneumoniae* GN118 | <0.025 | <0.025 | <0.025 | 0.78 | 0.05 |
| *Proteus rettgeli* GN624 | 0.10 | 0.05 | 0.10 | 1.56 | 1.56 |
| *Citrobacter froindii* GN346 | 6.25 | 6.25 | 6.25 | 50 | 12.5 |
| *Serratia marcescens* GN629 | 0.05 | 0.05 | 0.20 | 0.39 | 0.39 |
| *Pseudomonas aeruginosa* MB3833 | <0.025 | <0.025 | 0.39 | 0.78 | 12.5 |
| *Pseudomonas aeruginosa* IAM-1007 | <0.025 | <0.025 | 0.39 | 1.56 | 12.5 |

CAZ: Ceftazidime

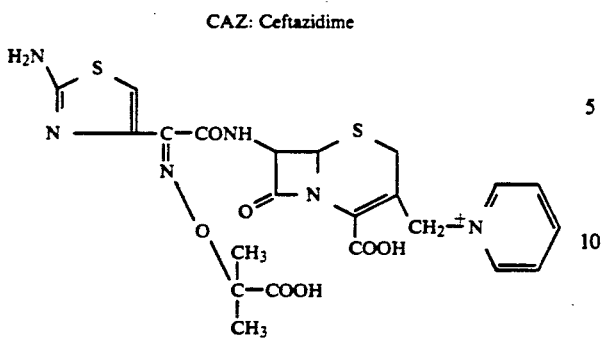

CTX: Cefotaxime

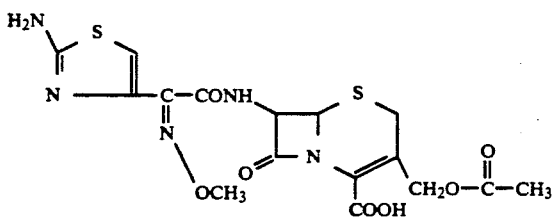

While the invention has been described in detail and with reference to specific embodiments thereof, it is apparent to one skilled in the art that various changes and modifications can be made therein without departing from the spirit and the scope of the present invention.

What is claimed is:

1. A cephalosporin compound having the formula:

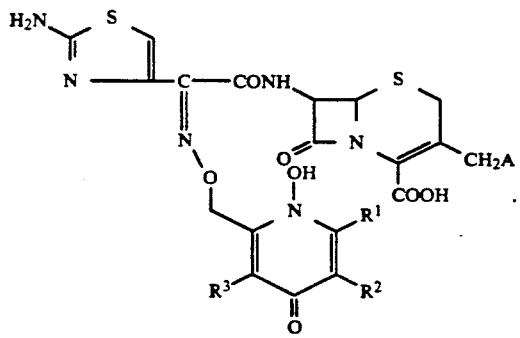

wherein $R^1$ represents a lower alkyl group, each of $R^2$ and $R^3$ independently represents a hydrogen atom or hydroxy group; and A represents a thiadiazolythio group of 1-methyltetrazolythio group or a pharmacologically acceptable salt or ester thereof.

2. An antibacterial composition comprising as the effective ingredient a cephalosporin compound having the formula:

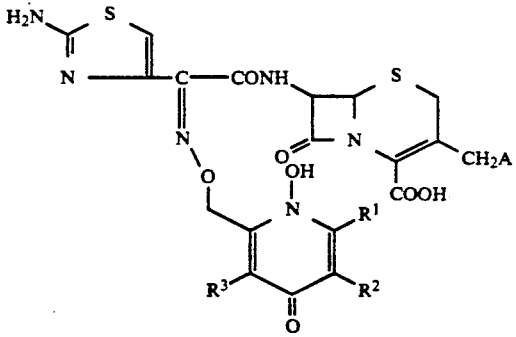

wherein $R^1$ represents a lower alkyl group; each of $R^2$ and $R^3$ independently represents a hydrogen atom or. hydroxy group and A represents a thiadiazolythio group or 1-methyltetrazolylthio group or a pharmacologically acceptable salt or ester thereof, and a pharmaceutically acceptable carrier therefor.

3. A compound as in claim 1, which is p-Methoxybenzyl 7-((Z)-2-2-tritylaminothiazol-4-yl)-2-(6-methyl-5-p-methoxybenzyloxy-1-diphenylmethyloxy-4-pyridon-2yl-methoxyimino)acetamido)-3(1,2,3-thiadiazol-5-ylthiomethyl)-3-cephem-4-carboxylate.

4. A compound as in claim 1, which is 7-((Z)-2-(2-Aminothiazol-4-yl)-2-(6-methyl-1,5-dihydroxy-4-pyridon-2-ylmethoxyimino)acetamido)-3-(1,2,3-thiadiazol-5yl-thiomethyl)-3-cephem-4-carboxylic acid.

5. A compound as in claim 1, which is Diphenylmethyl 7-((Z)-2-(2-tritylaminothiazol-4yl)-2-(6-methyl-5p-methoxybenzyloxy-1-diphenylmethyloxy-4-pyridon-2-yl-methoxyimino) acetamido)-3-(1-methyl-1H-tetrazol-5-ylthiomethyl)-3-cephem-4-carboxylate.

6. A compound as in claim 1, which is 7-((Z)-2-(2-Aminothiazol-4-yl)-2-(6-methyl-1,5-dihydroxy-4-pyridon-2-ylmethoxyimino)acetamido)-3-(1-methyl-1H-tetrazol-5-yltiomethyl) -3-cephem-4-carboxylic acid.

7. A compound as in claim 1, which is p-Methoxybenzyl 7-[(Z)-2-(2-tritylaminothiazol-4yl)-2-(5-p-methoxybenzyloxy-2-methyl-1-diphenylmethyloxy-4-pyridon-6-yl-methoxyimino)acetamido] -3-(1,2,3-thiadiazol-5-ylthiomethyl)-3-cephem-4-carboxylate.

8. A compound as in claim 1, which is 7-[(Z)-2-(2-aminothiazol-4yl)-2-(1,5-dihydroxy-2-methyl-4-pyridon-6-ylmethoxyimino)acetamido]-3-(1,2,3-thiadiazol-5-ylthiomethyl)-3-cephem-4-carboxylic acid.

9. A composition as in claim 2, wherein said compound is p-Methoxybenzyl 7-((Z)-2-(2-tritylaminothiazol-4yl)-2-(6-methyl-5-p-methoxybenzyloxy-1-diphenylmethyloxy-4-pyridon-2-yl-methoxyimino)acetamido)-3-(1,2,3-thiadizol-5-ylthiomethyl))-3-cephem-4-carboxylate.

10. A composition as in claim 2, wherein said compound is 7-((Z)-2-(2-Aminothiazol-4-yl)-2-(6-methyl-1,5-dihydroxy-4-pyridon-2-ylmethoxyimino)acetamido)-3-(1,2,3-thiadiazol-5-yl-thiomethyl)-3-cephem-4-carboxylic acid.

11. A composition as in claim 2, wherein said compound is Diphenylmethyl 7-((Z)-2-(2-tritylaminothiazol-4-yl)-2-(6-methyl-5-p-methoxybenzyloxy-1-diphenylmethyloxy-4-pyridon-2-yl-methoxyimino)acetamido)-3-(1-methyl-1H-tetrazol-5-ylthiomethyl)-3-cephem-4-carboxylate.

12. A composition as in claim 2, wherein said compound is 7-((Z)-2-(2-Aminothiazol-4yl)-2-(6-methyl-1,5-dihydroxy-4pyridon-2-ylmethoxyimino)acetamido)-3-(1-methyl-1H-tetrazol-5-ylthiomethyl) -3-cephem-4-carboxylic acid.

13. A composition as in claim 2, wherein said compound is p-Methoxybenzyl 7-[(Z)-2-(2-tritylaminothiazol-4yl)-2-(5-p-methoxybenzyloxy-2-methyl-1-diphenylmethyloxy-4-pyridon-6-yl-methoxyimino)acetamido]-3-(1,2,3-thiadiazol-5-ylthiomethyl)-3-cephem-4-carboxylate.

14. A composition as in claim 2, wherein said compound is 7-[(Z)-2-(2-aminothiazol-4-yl)-2-(1,5-dihydroxy-2-methyl-4-pyridon-6-ylmethoxyimino)acetamido]-3-(1,2,3-thiadizol-5-ylthiomethyl)-3-cephem-4-carboxylic acid.

15. A cephalosporin compound which is 7-((Z)-2-(2-amino-thiazol-4-yl)-2-(6-methyl-1,5-dihydroxy-4pyridon-2-ylmethoxyimino acetamido)-3-(1-methyl-1H-tetrazol-5-ylthiomethyl)-3-cephem-4-carboxylic acid.

* * * * *